United States Patent [19]
Kowalski et al.

[11] Patent Number: 5,559,728
[45] Date of Patent: Sep. 24, 1996

[54] CALIBRATION TRANSFER FOR SECOND ORDER ANALYTICAL INSTRUMENTS

[75] Inventors: Bruce R. Kowalski, Issaquah, Wash.; Yongdong Wang, Norwalk, Conn.

[73] Assignee: University of Washington, Seattle, Wash.

[21] Appl. No.: 237,368

[22] Filed: May 3, 1994

Related U.S. Application Data

[63] Continuation-in-part of Ser. No. 720,256, Jun. 24, 1991, Pat. No. 5,459,677, which is a continuation-in-part of Ser. No. 595,458, Oct. 9, 1990, abandoned.

[51] Int. Cl.$^6$ .................................................. G01N 21/01
[52] U.S. Cl. .................... 364/571.02; 73/1 R; 250/252.1
[58] Field of Search ......................... 364/571.01, 571.02, 364/571.04, 571.05, 497, 498; 73/1 R; 250/252.1

[56] References Cited

U.S. PATENT DOCUMENTS

| | | | |
|---|---|---|---|
| 4,587,624 | 5/1986 | Banno | 364/571.04 |
| 4,866,644 | 9/1989 | Shenk et al. | 364/571.02 |
| 5,121,337 | 6/1992 | Brown | 364/571.01 |
| 5,303,165 | 4/1994 | Ganz et al. | 364/571.01 |

OTHER PUBLICATIONS

Bruce E. Wilson, Eugenio Sanchez and Bruce R. Kowalski, "An Improved Algorithm for the Generalized Rank Annihilation Method," *Journal of Chemometrics*, vol. 3, 493–498 (1989).

Eugenio Sanchez and Bruce R. Kowalski, "Tensorial Calibration: II. Second–Order Calibration," *Journal of Chemometrics*, vol. 2, 265–280 (1988).

Eugenio Sanchez and Bruce R. Kowalski, "Tensorial Calibration: I. Second–Order Calibration," *Journal of Chemometrics*, vol. 2, 247–263 (1988).

Eugenio Sanchez, L. Scott Ramos and Bruce R. Kowalski, Generalized Rank Annihilation Method, "I. Application to Liquid Chromatography–Diode Array Ultraviolet Detection Data," *Journal of Chromatography*, 385, 151–164 (1987).

L. Scott Ramos, Eugenio Sanchez and Bruce R. Kowalski, Generalized Rank Annihilation Method, "II. Analysis of Bimodal Chromatographic Data," *Journal of Chromatography*, 385, 165–180 (1987).

Eugenio Sanchez and Bruce R. Kowalski, "Generalized Rank Annihilation Factor Analysis," *Analytical Chemistry*, vol. 58, No. 2, 496–499 (Feb. 1980).

*Primary Examiner*—James P. Trammell
*Assistant Examiner*—Edward Pipala
*Attorney, Agent, or Firm*—Christensen O'Connor Johnson & Kindness

[57] ABSTRACT

A method for calibrating two-dimensional responses measured on multiple instruments or on a single instrument under different operating conditions. The method calculates two separate banded diagonal transformation matrices using the responses of a common standard sample to simultaneously correct for the response channel shift and intensity variations in both dimensions or orders. The two transformational matrices are estimated from a set of simultaneous non-linear equations via the Gauss-Newton method. The effects of noise and transformation matrix bandwidth on the standardization performance were studied through computer simulation. From computer simulation and experimental data, it was found that the design of the standard sample is crucial for the parameter estimations and response standardization.

9 Claims, 9 Drawing Sheets

CALIBRATION TRANSFER FOR SECOND ORDER ANALYTICAL INSTRUMENTS

The present application is a continuation-in-part of pending and commonly owned, application U.S. Ser. No. 07/720, 256, filed Jun. 24, 1991, now U.S. Pat. No. 5,459,677, which is hereby incorporated in its entirety by reference, which is a CIP of U.S. Ser. No. 07/595,458 filed Oct. 9, 1994, now abandoned.

FIELD OF THE INVENTION

The present invention relates to techniques for the calibration of second order analytical instruments such as gas chromatography mass spectrometers (GCMS) and liquid chromatography ultraviolet spectrometers (LCUV).

BACKGROUND OF THE INVENTION

The analytical chemist is frequently confronted with the problem of analyzing a sample to identify one or more properties of the sample, such as the octane number of a gasoline sample, or the protein content of a wheat sample. A closely related problem is the analysis of a sample to identify some or all of its constituents, and to determine their concentrations. The concentration of a given constituent can be regarded as a chemical property of the sample.

On many occasions, an instrument such as an absorption spectrophotometer is used to analyze the sample. However, instruments respond with signals (e.g., voltages or current), not reports of properties. Therefore, a relationship has to be built that relates responses to properties before the instrument can be used to analyze samples. The process of building a model for the prediction of the properties of a sample from the instrument's response is called calibration.

The advantages flowing from a successful model can be considerable. Imagine, for example, that it is desired to measure the concentration of a certain chemical species (analytes) in a chemical process stream. The most direct measurement technique would be to extract a sample from the process stream, and subject the sample to traditional chemical analysis techniques, to determine the analyte concentration. However, such an approach is cumbersome, and does not provide real time information. If a model could be constructed that relates the unknown concentration to absorbence of light at one or more wave lengths, a significant simplification would result. Concentration could then be estimated by placing a suitable optical absorbence measuring device in the process stream itself, thereby providing an efficient and real time technique for estimating the analyte's concentration.

An example of a calibration model is a classical calibration curve. The responses of an instrument are measured with a set of standard samples (calibration standards) of known analyte concentrations. Such a set of calibration standards will be referred to herein as a calibration set. If a linear model is appropriate, then the response r measured by the instrument can be written $$r = b_1 c + b_0$$

where c is the concentration of the analyte of interest, and the constants $b_1$ and $b_0$ are the model parameters. This task is a univariate problem, in that the instrument response r is assumed to be a function of a single variable c. To calibrate the instrument, the instrument response r is measured for each sample in the calibration set, each such sample having a known concentration c. A linear least squares regression technique may then be used to determine the values of the constants $b_1$ and $b_0$ that provide the best fit of the above equation to the measured data. Once the model parameters are determined, concentrations of future samples may be estimated from the model, based upon the measured instrument response r.

Such univariate calibration requires that the instrument response be dependent only on the concentration of the analyte of interest. In order to fulfill this condition, the analytical chemist must separate the analyte from other constituents of the sample that interfered with the instrument response or use a highly selective instrument. Thus, classical univariate calibration demands that the chemist make certain that there are no interfering species. If inadvertently, an interfering constituent is present, there is no way to detect the error, much less to correct it.

Unfortunately, it is rarely possible to find univariant models that provide useful real world information. For example, it is generally the case that light absorbence at any given wavelength is affected by many chemical species that may be present, by turbidity, etc. In this more common case, the problem is multivariate, i.e., the measurable absorbance is a function of multiple variables, and multivariate calibration must be used to obtain reliable estimates of the property of interest. The use of multivariate calibration of analytical instruments is a rapidly growing field, primarily due to the development of so-called biased multivariate regression methods, such as principal component regression (PCT) and partial least squares (PLS).

Figure 1A:
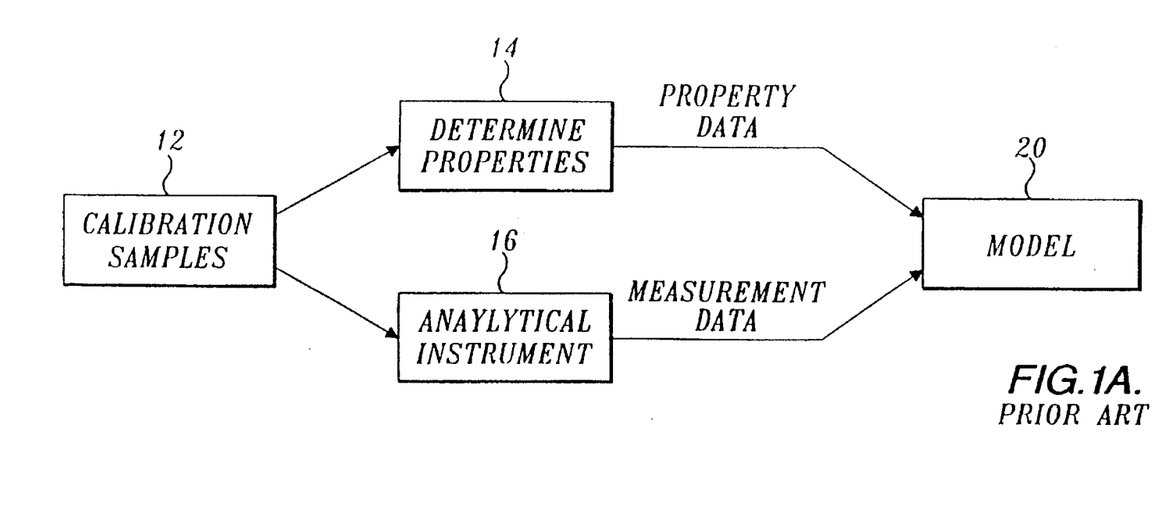
FIGS. 1A and 1B generally illustrate the prior art process of constructing a multivariant model from a set of calibration samples, and using the model to predict the properties of an unknown sample.
Figure 1B:
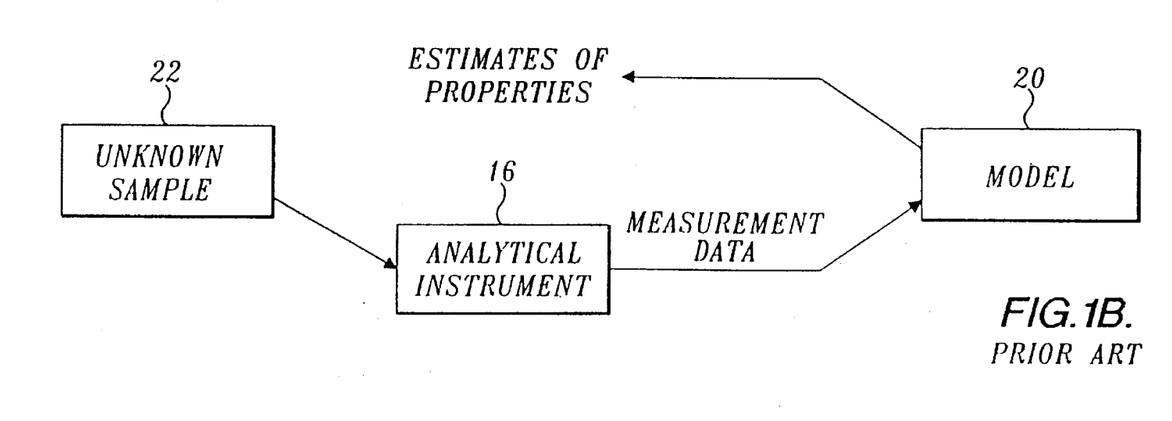

A standard multivariate calibration technique (prior art) is illustrated in schematic form in FIGS. 1A and 1B; the technique begins with the preparation of a plurality of calibration samples 12. The calibration samples are formulated such that they are typical examples of the material, e.g., sampled from the process stream which the model will be used to analyze. One or more properties of interest for each calibration sample are then determined, as indicated in a block 14, to produce "property" data representing such properties. In the case of a physical property such as octane number, an analytic technique of accepted reliability and accuracy is used to measure the octane number for each calibration sample. In the case where the properties are the concentrations of different chemical species, the concentrations may simply be recorded during the preparation of the samples. One then performs a plurality of measurements of each calibration sample, using an analytical instrument 16, to produce "measurement" data. For example, for the case in which the analytical instrument is a spectrophotometer, the absorbence of each sample is measured at a plurality of different wavelengths. Then, using any multivariate calibration method (e.g., principal component regression, partial least squares regression), one combines the property data produced in step 14 with the measurement data produced by analytical instrument 16, to obtain a model 20, i.e., a mathematical relationship, between the measured absorbencies and the property or properties of interest. Once model 20 has been created, it can be used to estimate the property or properties of an unknown sample, as shown in FIG. 1B. In particular, the unknown sample is analyzed using analytical instrument 16 (the same instrument shown in FIG. 1A), to produce measurement data that are input to model 20. The model produces an estimate of the property or properties of the unknown sample.

While the above described multivariate calibration technique is very powerful, a significant limitation of the technique has recently been recognized. This limitation is based upon the fact that no two analytical instruments are precisely identical to one another, even instruments of the same type coming from the same manufacturer. Thus, a calibration model determined using a first instrument cannot generally be used for other instruments of the same type, without a significant loss of accuracy. The ideal way to avoid this problem would be to calibrate each individual instrument, using all of the samples in the calibration set. However, complete calibration of each instrument is impractical in many situations. Complete recalibration, for example, could often require the transportation of a large number of calibration samples to the site of each instrument, a challenging task when the samples are numerous, chemically or physically unstable, or hazardous. It would therefore be highly useful to develop techniques for transferring a calibration model derived for a first, reference instrument for use on a second target instrument.

A closely related problem occurs when the responses measured on a single instrument change over a period of time for any reason, for example, temperature fluctuations, electronic drift, wavelength or detector instability, etc. If such changes occur after the development of a calibration model, then subsequent use of the model may produce erroneous results. Conceptually, the problem of differences between instruments is nearly identical to the problem of variation of a single instrument over time, although they are associated with different causes. Both problems involve calibration on a reference instrument, and an attempt to use the calibration model on a target instrument that produces responses that differ from those of the reference instrument in some way. The target instrument may be either the same instrument at a later time, or a different instrument. A copending and commonly owned application, U.S. Ser. No. 07/720,256 now U.S. Pat. No. 5,459,677, describes a method of calibration transfer for instruments that provide a response dependent upon a single parameter or property. However, for other types of instruments such as a gas chromatography mass spectrometers (GCMS) or liquid chromatography ultraviolet spectrometers (LCUV), which provide responses that are dependent upon two properties or parameters of the material to be analyzed, a more complex calibration transfer method and apparatus is necessary. However, the copending application, Ser. No. 07/720,256, now U.S. Pat. No. 5,459,677, provides background and foundation material for use in understanding the present invention and is hereby incorporated in its entirety by reference.

SUMMARY OF THE INVENTION

A method for standardizing two-dimensional responses measured on multiple instruments or on a single instrument under different operating conditions is disclosed. The method calculates two separate banded diagonal transformation matrices using the responses of a common standard sample to simultaneously correct for the response channel shift and intensity variations in both dimensions or orders. The two transformational matrices are estimated from a set of simultaneous non-linear equations via the Gauss-Newton method. The effects of noise and transformation matrix bandwidth on the standardization performance are studied through computer simulation. From computer simulation and experimental data, it has been found that the design of the standard sample is crucial for the parameter estimations and response standardization.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

DETAILED DESCRIPTION OF THE PREFERRED EMBODIMENT

As noted above, in the copending commonly owned application, Ser. No. 07/720,256, now U.S. Pat. No. 5,459,677, a method and apparatus for multivariate calibration was developed for first order instruments (e.g., spectrometers) that produce a vector of data per sample. However, the method and apparatus disclosed in that application was not intended nor completely suitable for use on second order instruments that are capable of generating a matrix of data for each sample analyzed. Though providing more information on a sample in terms of analytical capacity, second order instruments are more prone to response variations, which can occur in both properties or parameters (orders) simultaneously. For example, the second order data collected from liquid chromatography with ultraviolet spectroscopic detection may have a shift in retention time, due to temperature and pressure fluctuations and column aging, as well as a wavelength shift in the UV spectrometer and a spectroscopic intensity variation, due to the misalignment of the monochrometer and light source intensity changes. Further, when such instrumental variations occur in second order data, it is difficult to decide whether the variations come from one order or the other order or both orders.

One approach would be to use the methods disclosed in our copending application separately on each order. It would then be necessary to assume that one order is stable while the other order is being standardized. However, because it is difficult to determine whether or not the variations occur in only one order or both orders simultaneously, it is extremely difficult to apply the methods of first order calibration transfer disclosed in the copending application to standardize a second order instrument.

In the present invention, a general second order calibration transfer method is disclosed that operates on both orders simultaneously to achieve second order calibration transfer. Though second order calibration transfer is the primary thrust of the present invention, the present invention can be used for other purposes such as interlaboratory comparison and validation of second order instruments, which has heretofore been an extremely difficult task.

In first order piecewise direct standardization (PDS) as discussed in the above-referenced copending application and also in Y. Wang et at., *Anal. Chem.* 63:2750, 1991, the responses of a small set of transfer samples measured on two different instruments are related to one another through a banded diagonal matrix F (for continuous responses), $$\bar{R}_1 = \bar{R}_2 F \tag{1}$$

where $\bar{R}_1$ and $\bar{R}_2$ are the matrices containing instrument responses in the rows. This banded diagonal matrix F is arranged in such a way that the response at every specific channel on the first instrument can be represented as a linear combination of the responses in a small window near this specific channel on the second instrument. The linear combination can accomplish corrections of both response channel shifts and intensity changes.

However, with second order instruments that provide a response or output that is a matrix, $N_1$ (dimensioned m×n), a different approach is necessary. Specifically, when $N_1$ measured on one instrument is compared to an $N_2$ (dimensioned the same as $N_1$) on a another instrument (measuring the same sample), it is expected that differences will occur in both orders. To correct for such complicated variations, two transformation matrices similar to F are needed. This requirement leads to the following nonlinear form in which the responses of the common sample from both instruments are related to one another via a left and right transformation matrix, A and B, $$N_1 = AN_2B \tag{2}$$

The left transformation A will correct for shift and intensity differences between the rows of $N_1$ and $N_2$ (e.g., standardizing the LC order on a LCUV spectrometer) with the following banded diagonal form $$A = \begin{bmatrix} a_1^T & & & \\ & a_2^T & & 0 \\ & & \cdot & \\ & & & \cdot \\ 0 & & & \cdot \\ & & & a_p^T \end{bmatrix} \tag{3}$$

where $a_i$ (i=1,2, . . . , p) is a short column vector. The right transformation B will correct for shift and intensity differences between the columns of $N_1$ and $N_2$ (e.g., standardizing the UV order on a LCUV) with the following banded diagonal form $$B = \begin{bmatrix} b_1 & & & \\ & b_2 & & 0 \\ & & \cdot & \\ & & & \cdot \\ 0 & & & \cdot \\ & & & b_q \end{bmatrix} \tag{4}$$

where $b_j$ (j=1,2, . . . , q) is also a short column vector. Thus, for a second order instrument, matrix A corrects for the first order and matrix B corrects for the second order.

In Equation 2, the left transformation A is dimensioned as p×m, and the right transformation B is dimensioned as n×q, where p≤m and q≤n. The standardized response $N_1$ is thus dimensioned as p×q, with the first and last several rows and columns (referred to as missing ends) properly deleted or extrapolation employed. The selection of p and q is directly related to the bandwidth in A and B and confined by both the rank of $N_1$ or $N_2$ and their original dimensions (m and n). This point will be addressed in greater detail below as well as a discussion on a numerical solution for A and B and their uniqueness.

Once A and B have been determined from the responses $N_1$ and $N_2$ of a common standard sample, any future response $M_2$ measured on the second instrument can be standardized into the response $M_1$ as if it had been measured on the first instrument using $$M_1 = AM_2B \tag{5}$$

With $M_1$, this sample can be combined with all other (calibration) samples measured on the first instrument, fix the purpose of either second order calibration, library searching, classification, or identification.

In the search for a numerical solution for A and B in Equation 2, an iterative alternating least squares procedure was initially used, based on the fact that Equation 2 can be reduced to a first order standardization problem when either A or B is known. The iteration starts by setting, for example, the left transformation A, as an identity matrix, and uses the first order PDS disclosed in the above-referenced copending commonly owned application to calculate the right transformation B, which is then inserted into Equation 2 to standardize from the right hand side. This standardized response can now be used in another first order PDS to calculate an update for the left transformation A. This cycle can be repeated until convergence occurs. Unfortunately, while the iteration does converge, it has been determined that the iteration does not converge to the optimal and correct solution. This result indicates that the two orders cannot be standardized separately, even in an alternating fashion, and that a simultaneous solution for both A and B is needed.

It is insightful to write out the expression for a typical element in $N_1$, $N_{1,ij}$, as a function of a corresponding local submatrix of the elements in $N_2$ by the use of Equation 2

$$N_{1,ij} = a_i^T \bar{N}_2 b_j \tag{6}$$

where $a_i^T = [A_{ii-u} A_{ii-u+1} \ldots A_{ii+v-1} A_{ii+v}]$ $b_j = [B_{j-r,j} B_{j-r+1,j} \ldots B_{j+s-1,j} B_{j+s,j}]^T$ represent the nonzero elements along the banded main diagonals of A and B, respectively, and $\bar{N}_2$ is a $(u+v+1) \times (r+s+1)$ submatrix of $N_2$ $$\bar{N}_2 = \begin{bmatrix} N_{2,i-uj-r} & \ldots & N_{2,i-uj+s} \\ \cdot & \cdots & \cdot \\ \cdot & \cdots & \cdot \\ \cdot & \cdots & \cdot \\ N_{2,i+vj-r} & \ldots & N_{2,i+vj+s} \end{bmatrix} \tag{7}$$

Now it becomes clear that in the second order standardization given by Equation 2, a rectangle in response matrix $N_2$ is constructed around each corresponding element in $N_1$ and the left and right transformation vectors, $a_i$ and $b_j$, are estimated such that Equation 6 is satisfied in a least squares sense. Recalling that in first order calibration, a small window is constructed on the second instrument near each specific response channel on the first instrument, the second order standardization is a two-dimensional version of PDS. Unlike in first order PDS, however, all rectangles in two-dimensional PDS are connected with one another through different left and right transformation vectors. For example, $a_i$ appears in the expressions for all elements on the ith row of $N_1$, and $b_j$ appears in the expressions for all elements on the jth column of $N_1$. As a result, a numerical solution similar to the moving window method in first order PDS cannot be devised to produce overall least squares estimations for these two transformations.

A nonlinear least squares method is presented to solve for all nonzero parameters in A and B simultaneously. The numerical procedure used is the Gauss-Newton method (see e.g. J. E. Dennis, Jr., *Nonlinear Least-Squares, State of the Art in Numerical Analysis*, D. Jacobs, Ed., Academic Press, p. 269–312, 1977; The Math Works Inc., *Optimization Toolbox (for use with MAYLAB™)*, South Natick, Mass., 1991), which requires explicit expressions for first derivatives of all elements in $N_l$. From Equation 6, these first derivatives can be derived as $$\frac{\partial N_{1,ij}}{\partial A_{i\zeta}} = \sum_{t=i-u}^{i+v} N_{2,\zeta t} B_{tj}$$

where $\zeta \in [i-u, i-u+1, \ldots, i+v-1, i+v]$, and $$\frac{\partial N_{1,ij}}{\partial B_{\zeta j}} = \sum_{t=i-u}^{i+v} N_{2,t\zeta} A_{it}$$

where $\zeta \in [j-r, j-r+1, \ldots, i+s-1, i+s]$.

For the elements in the first u rows, last v rows, first r columns, and last s columns of $N_1$, the rectangle in Equation 7 cannot be constructed. These elements are therefore ignored in the nonlinear least squares estimation described above. Alternatively, an extrapolation procedure may be employed. Thus the valid ranges for i and j in Equation 6 are $u+1 \leq i \leq m-v$ and $r+1 \leq j \leq n-s$, respectively. As a result, p and q in Equations 3 and 4 are given by $p=m-u-v$ and $q=n-r-s$. It should be pointed out that although a constant bandwidth is assumed fox both A and B in the above derivation, A and B can in fact have varying bandwidths, as long as the uniqueness condition to be discussed in the next section is satisfied.

The uniqueness of the nonlinear least squares solution for A and B is dependent on the bandwidths in A and B and the dimensionality of $N_1$ and $N_2$. According to the formulation in the previous sections, the total number of unknown parameters (nonzero elements) in A and B is $p(u+v+1)+q(r+s+1)$. In Equation 2, the absolute magnitude of the elements in A and B is undetermined. For example, A can be scaled up by a factor, while B can be scaled down by the same factor without changing the least squares fit of Equation 2. Thus in the calculation, an element of A is held constant, for example, by setting $A_{11} \propto 1$. Though there are $p \times q$ usable elements in $N_1$, the number of independent elements in $N_1$ is limited by its rank and is given as $rank(N_1) \times max(m,n)$. Therefore, a necessary and sufficient condition for the uniqueness of a solution is given by the following inequality $$p(u+v+1)+q(r+s+1)-1 \leq rank(N_1) \times max(m,n) \tag{8}$$

For example, when $m=n=10$ and $u=v=r=s=1$ (i.e., A and B are banded diagonal matrices each with one super-diagonal and one sub-diagonal), the uniqueness condition is $rank(N_1) \geq 5$. In the case of an LCUV experiment, this condition means that a five component mixture needs to be injected as the standard sample, in order to correct for both retention time and spectral wavelength shift in a range from $-1$ to $+1$ unit.

Equation 8 implies that second order standardization can be accomplished with only one sample, preferably a complicated sample with high rank. Compared to first order standardization where multiple standard samples are required, this conclusion may be considered as one additional second order advantage. When more standard samples are available for standardization, the second order standardization will be improved. In this case, more equations similar to Equation 2 can be included in the nonlinear least squares estimation, or the sum of all standard samples can be used to replace $N_1$ and $N_2$. Since this summed "sample" has a higher signal to noise ratio and possibly a higher rank than $N_1$ alone, it is expected that Equation 2 will become more over-determined, and the nonzero parameters in A and B can be better estimated.

In case multiple bilinear second order spectra are available for standardization, there is an alternative approach to calculate the left and right transformations. A trilinear decomposition (see e.g. E. Sanchez and B. R. Kowalski, *Chemometrics* 4:29, 1990) can be applied to multiple bilinear samples to obtain the resolved pure component spectra X and Y in both orders. Assuming two bilinear samples (M and N) are measured on the first instrument as $M_1$ and $N_1$, which can be decomposed as $$M_1 = X_1 C_M Y_1^T$$

$$N_1 = X_1 C_N Y_1^T$$

where $C_M$ and $C_N$ are both diagonal matrices with the analyte concentrations in M and N on the diagonals. When the same two samples are measured on the second instrument, the responses $M_2$ and $N_2$ can be similarly decomposed as $$M_2 = X_2 C_M Y_2^T$$

$$N_2 = X_2 C_N Y_2^T$$

It is seen that the instrumental differences in the X order are represented by $X_1$ and $X_2$ while the differences in the Y order are represented by $Y_1$ and $Y_2$. Consequently, the left and right transformations A and B can be calculated via two separate first order standardizations as follows $$X_1^T = X_2^T A^T$$

$$Y_1^T = Y_2^T B$$

For the same example as given above, a sufficient condition for the uniqueness is rank($X_1$)=rank($X_2$)=rank($Y_1$)= rank($Y_2$)≧3, which requires less complicated standard samples containing only three components.

Figure 2:
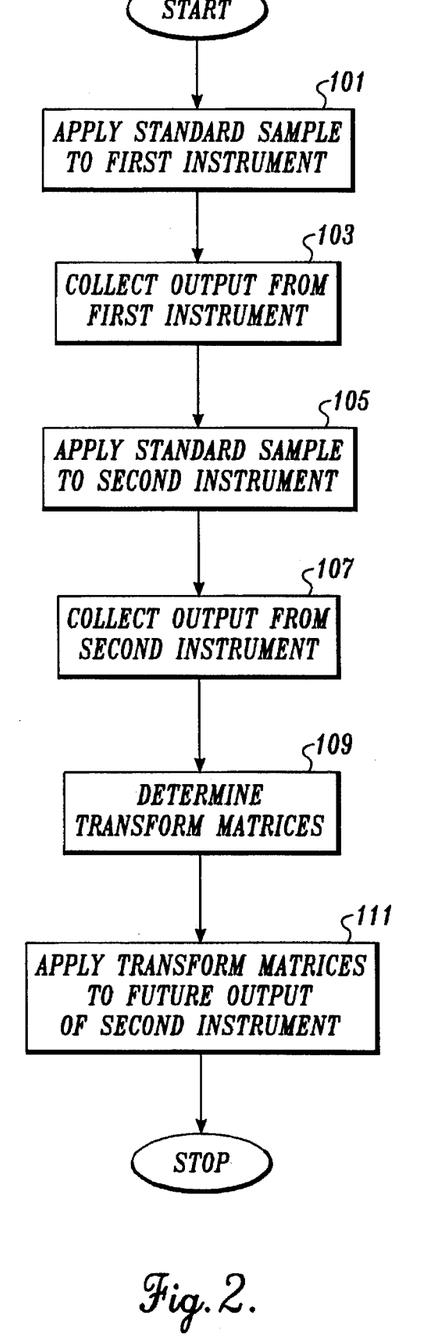
FIG. 2 is a diagram illustrating the method of the present invention.

The implementation of the method of the present invention can be seen in FIG. 2. In this particular application of calibrating a second instrument to a first instrument, first at box 101, a standard sample is provided to the first instrument for analysis. The standard sample should have sufficient components to provide for adequate calibration as discussed above. Next, at box 103, the output of the first instrument is recorded. The standard sample at box 105 is then provided to the second instrument for analysis. At box 107, the output of the second instrument is recorded. Next, at box 109, the transformation matrices are determined using, in the preferred embodiment, the non-linear least squares method. Finally, at box 111, the transformation matrices are applied to all future output of the second instrument. In the above manner, the output of the second instrument has been calibrated to the first instrument.

To aid in the confirmation of the present method, a computer simulation was used. The chromatograms and spectra for nine components were generated using Gaussian peaks. Seven out of these nine components were used to generate a bilinear response matrix N $$N = \sum_{i=1}^{7} c_i x_i y_i^T$$

where $x_i$'s and $y_i$'s are the vectors containing pure chromatograms and spectra for these seven components, and $c_i$'s are their corresponding concentrations. The remaining two components were combined with two of the components included in N to form another bilinear response M $$M = \sum_{i=6}^{9} c_i x_i y_i^T$$

Figure 3:
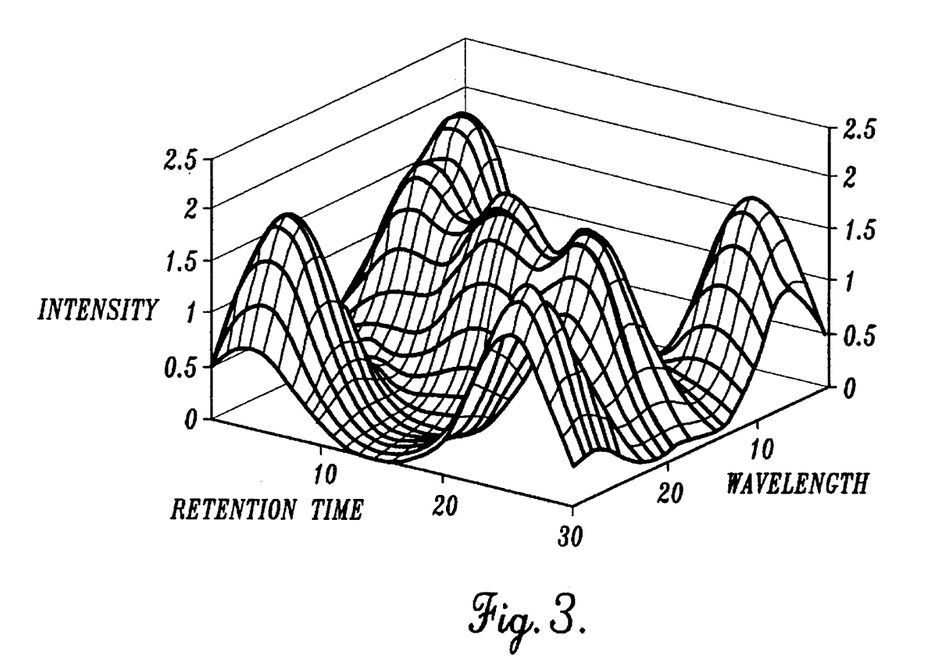
FIG. 3 is a simulated standard sample response from a first instrument.
Figure 4:
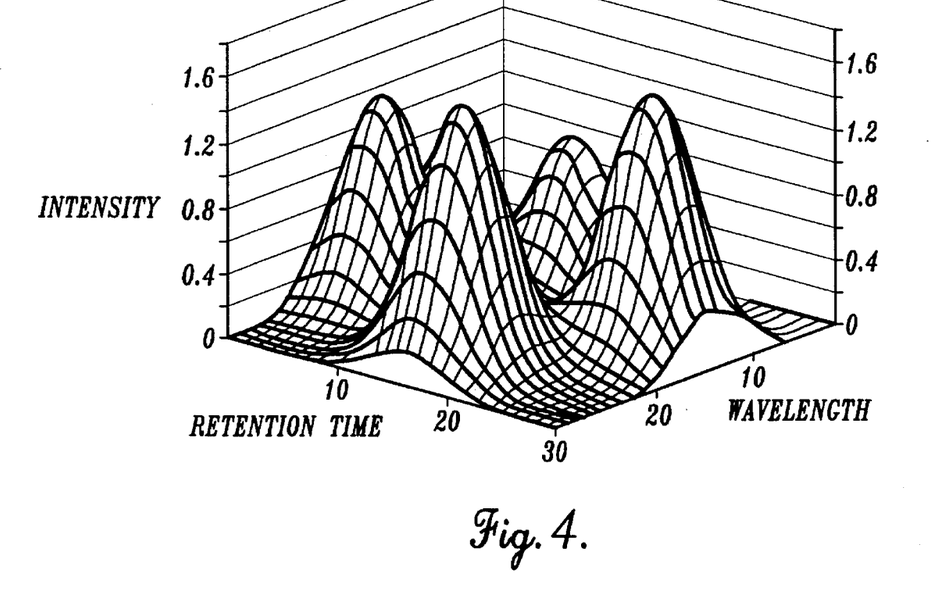
FIG. 4 is a simulated test sample response from the first instrument.

To simulate a deviation from the Lambert-Beer Law, the following transformation (see e.g. P. J. Gemperline et al., *Anal. Chem.* 63:2313, 1991) was carried out for every element in N and M to generate the true responses $N_1$ and $M_1$ on the first instrument (plotted in FIGS. 3 and 4 respectively), $$N_{1,ij} = -\log(e^{-N_{ij}} + 0.01) \quad (9)$$

and $$M_{1,ij} = -\log(e^{-M_{ij}} + 0.01) \quad (10)$$

Figure 5:
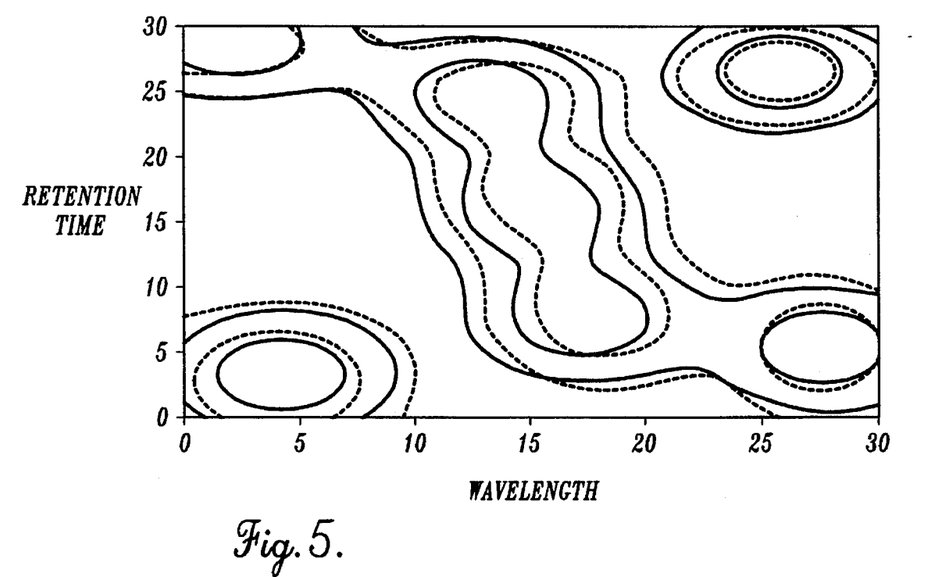
FIG. 5 is a contour plot of simulated standard sample responses on the first instrument (solid line) and a second instrument (dashed line)
Figure 6:
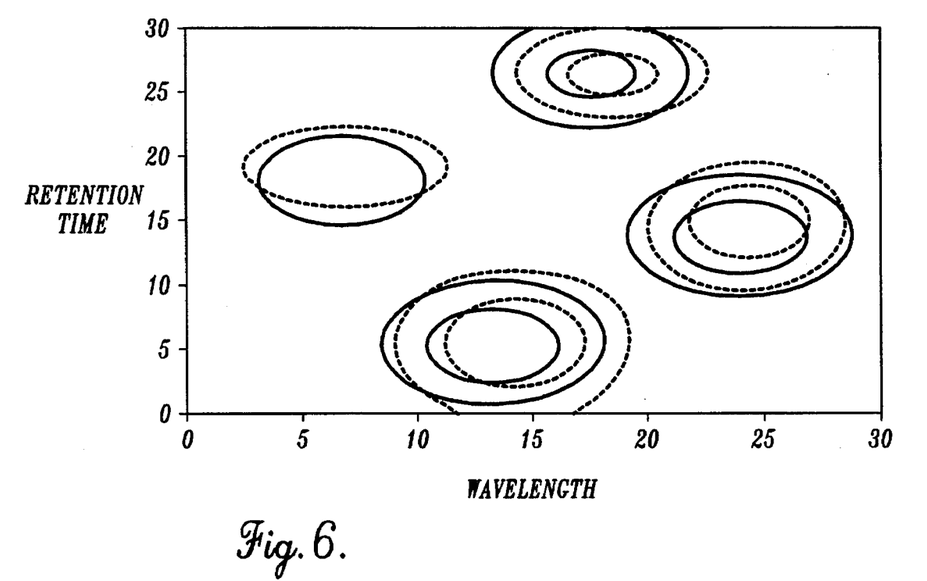
FIG. 6 is a contour plot of simulated test sample responses on the first instrument (solid line) and the second instrument (dashed line)

The responses on the second instrument were simulated through a nonlinear shift of both the chromatographic and spectral axes. This nonlinear shift was generated using a quadratic form $a+bx+cx^2$, where the parameters a, b, and c were determined such that the shift at both ends was −1 while that at the extrema was +1 unit. N and M were subjected to this shift with linear interpolation to generate the bilinear responses on the second instrument. Following a 10% linear intensity gain, a nonlinear intensity change (approximately 10% of the linear intensity) was simulated by adding 0.03, instead of 0.01, in Equations 9 and 10 to generate the true responses $N_2$ and $M_2$ on the second instrument. The responses from the two instruments are overlaid in the contour plots shown in FIGS. 5 and 6. It is seen that there are significant intensity changes and complicated response channel shifts from one instrument to the other.

In the simulation, $N_1$ and $N_2$ were used as the standard sample responses while $M_1$ and $M_2$ were used as the test sample responses. Six noise levels, 0.00%, 0.05%, 0.10%, 0.50%, 1.00%, and 5.00%, and eight different types of bands for A and B were tested in a full factorial design with 5 repetitions. Since the simulated nonlinear shift was symmetrical in both orders, the same sized band was used for A and B. In each simulation, A and B were estimated from the standard sample responses on both instruments and a residual matrix was calculated for Equation 2 which indicates the accuracy of the model. From this residual matrix, a modeling error was calculated as the mean of the standard deviations of all elements. Similarly, a standardization error could be calculated from the residual matrix for Equation 5 with the estimated A and B. To measure the stability of the proposed parameter estimation method, a standard deviation was also calculated for A and B, which is the mean standard deviation of all elements in the estimated A or B (as compared to the A and B calculated at 0.00% noise level).

Figure 7:
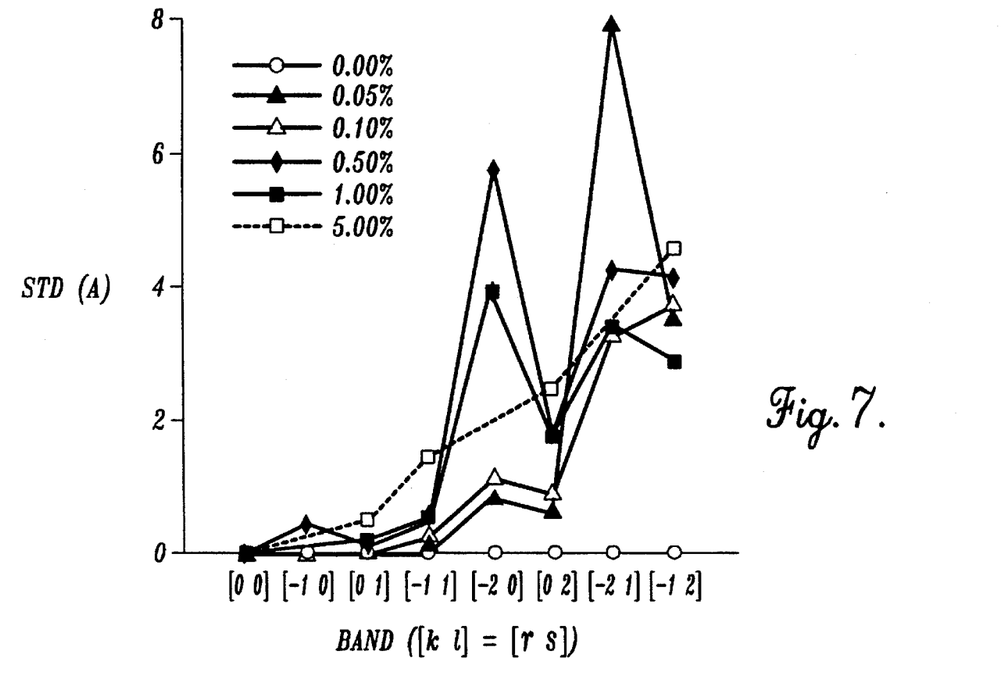
FIG. 7 is a chart of the mean standard deviation in the estimation of a first transformation matrix A at different noise levels.
Figure 8:
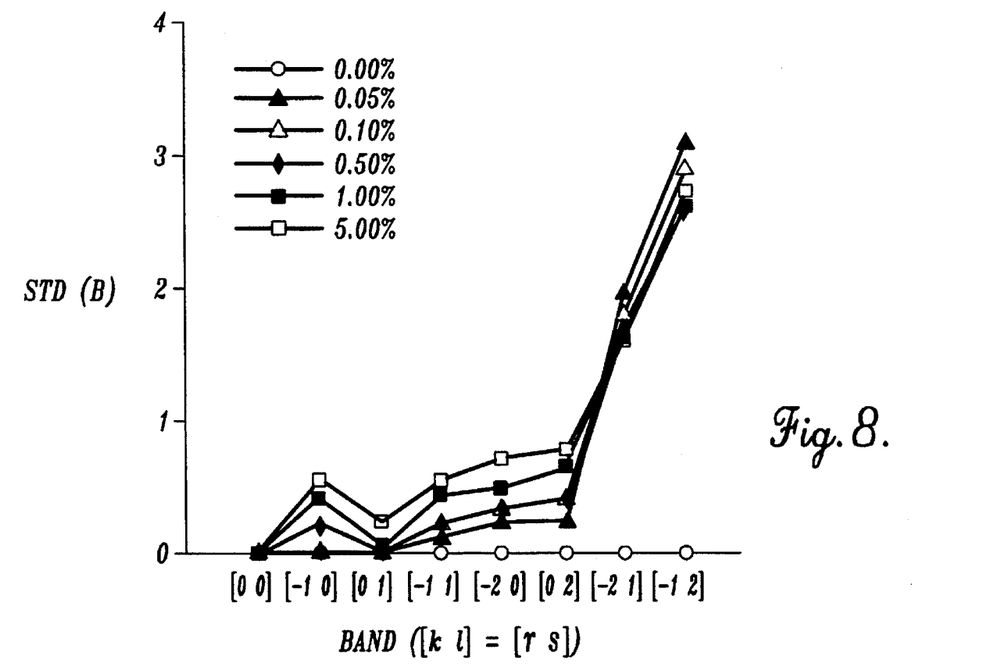
FIG. 8 is a chart of the mean standard deviation in the estimation of a second transformation matrix B at different noise levels.

The averaged standard deviations in the estimation of all the nonzero elements in the left and right transformations, A and B, are plotted in FIGS. 7 and 8, respectively. From these two figures, it can be seen that more stable estimates of A and B are obtained with smaller bandwidths, a result that corresponds to a more over-determined nonlinear system. This result is consistent with the discussion presented in the theory section, suggesting that a smaller bandwidth is always preferred in terms of parameter estimation. When the band increases to [−2 1] and [−1 2], the mean standard deviation of A and B undergoes a significant increase, indicating some fundamental change in the system described by Equation 2. In fact, referring back to the uniqueness discussion, it is seen that Equation 8 is no longer satisfied in these two cases. It is expected that during the parameter estimation the standard deviation will approach infinity, which surprisingly, is not the case in FIGS. 7 and 8. This contrary result is believed to be related to the fact that a nonlinearity of the form in Equations 9 and 10 was added and the effective rank of the response matrix was slightly increased.

When the noise effect is considered, it is seen that the parameter estimation for A is relatively stable in the range of 0.00%–1.00% noise, while the estimation for B seems to be stable in the whole noise range tested (from 0.00%–5.00%). When FIG. 7 is compared to FIG. 8, a much more dramatic fluctuation in A is observed. In fact, this fluctuation in A is so dramatic at the 5.00% noise level that some of the points had to be left out of the figure. After careful examination, it is found that this dramatic variation comes from the rows in A corresponding to the retention times around 13. Referring back to FIG. 3, it is seen that there is only one dominant peak in this region of the response. As a result, the local rank of the response in this region is significantly smaller than the overall rank, which determines the uniqueness of parameter estimation, especially when the noise level in the data is high. This relationship between the local rank and overall rank explains the poor parameter estimation in A at high noise levels. The components are distributed much more evenly along the wavelength axis, and the parameter estimation in B becomes more stable. In light of this observation, the standard sample for second order standardization should be designed in such a way that not only the overall rank satisfies the uniqueness of Equation 8, but also the local ranks (when examined from both orders) approach this overall rank as much as possible. In other words, the different components in the standard sample should be evenly spread out in the x-y plane.

Figure 9:
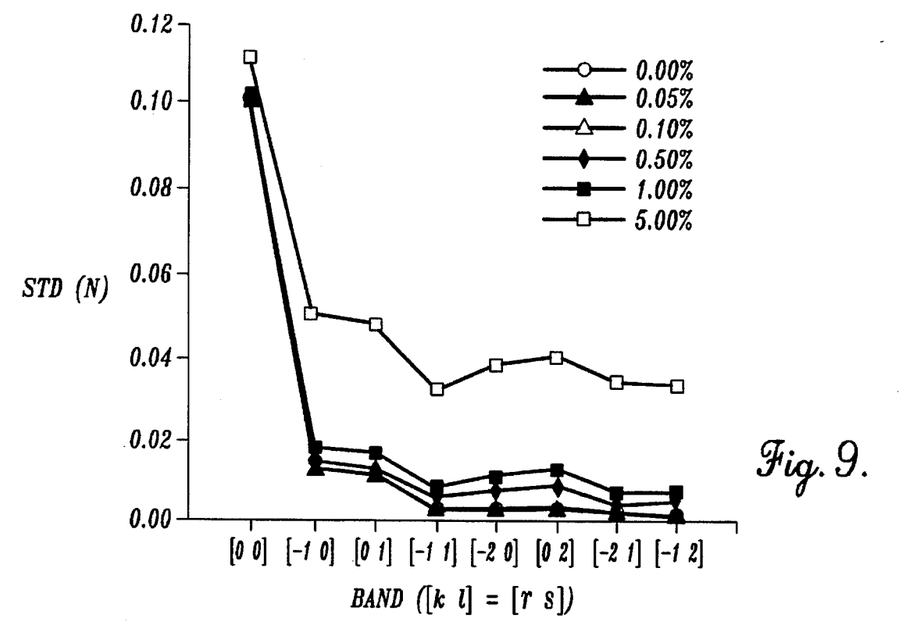
FIG. 9 is a chart of the mean standard deviation in matching the response of the standard sample from the second instrument to the first instrument at different noise levels.

The modeling error calculated for the standard sample is plotted in FIG. 9. In FIG. 9, the large error at band=[0 0] indicates that a sufficient standardization model has not been obtained. The simulated nonlinear shift is in the [−1 1] range, along with the nonlinear intensity change from instrument to instrument. When one more nonzero diagonal is included in the standardization (at band=[−1 0] and [0 1]), the modeling error is significantly reduced. It is interesting to note that the modeling errors at band=[−1 0] and [0 1] are comparable to each other, showing some form of symmetry. This symmetry is consistent with the fact that the shift range is actually [−1 1]. At band=[−1 1], the modeling error is further reduced at all noise levels. At the same bandwidth with band=[−2 0] and [0 2], the modeling errors increase only slightly. This small increase suggests that the correction estimation of the range of shifts in A and B is not critical owing to the continuity of the responses. When the bandwidth is overestimated by one with the range of shifts included (at band=[−2 1] and [−1 2]), the modeling error is only slightly reduced, indicating that a smaller bandwidth is sufficient to correct for both the nonlinear shifts and nonlinear intensity changes. The symmetry in the modeling error at band={[−2 0], [0 2]} and {[−1 2], [−2 1]} is also observed. As for the noise sensitivity, it is seen that the modeling error increases slowly as the noise increases from 0.00% to 1.00%. From 1.00% to 5.00% noise, the modeling error is significantly increased, due mostly to the large variance in the estimation of A, as has been discussed above. Nonetheless, this can be improved through a better designed standardization sample.

Figure 10:
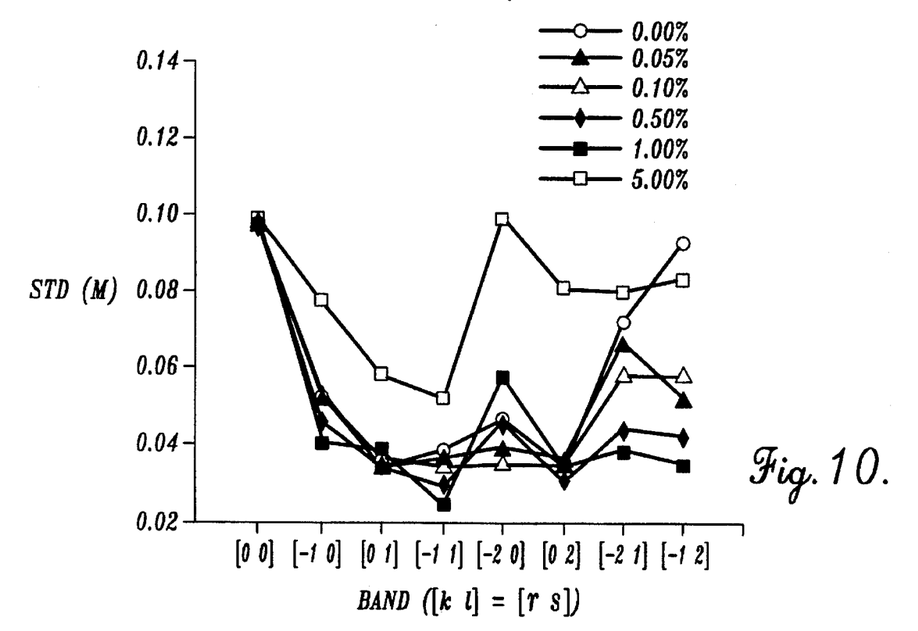
FIG. 10 is a chart of the mean standard deviation in matching the response of the test sample from the second instrument to the first instrument at different noise levels.

The standardization error calculated from the test sample (FIG. 10) shows a pattern similar to that in FIG. 9. One difference is that the magnitude of the standardization error is about two times that of the modeling error, since the former is prediction error, while the latter is just fitting error. Another difference is that the error increases dramatically when the band reaches [−2 1] and [−1 2], especially at higher noise levels, indicating the occurrence of overfitting when an overly large bandwidth is used. In the noise range from 0.00%–1.00%, the standardization error is relatively stable from band=[−1 0] to [0 2]. This stability is consistent with the discussion above. The standardization error in this range is around 0.04 absorbance unit, which is quite acceptable considering the pronounced difference seen from FIGS. 5 and 6. The variation pattern of the standardization error at the 5.00% noise level and at band=[−2 1] and [−1 2] is more complicated and less interpretable, due to the enormous variation in the estimation of A at the 5.00% noise level (FIG. 7) and the large variation in the estimation of both A and B at band=[−2 1] and [−1 2] (FIG. 8). Again, this result can be improved by using a better designed standard sample.

To further evaluate the method of the present invention, a LCUV experiment was conducted. In the LCUV experiment, a reversed phase HPLC system was connected to a Hewlett-Packard (Palo Alto, Calif., U.S.A.) 8452A Diode Array Spectrometer via a flow-through cell. The mobile phase consisted of 60% methanol and 40% 0.005M tetrabutylammonium sulfate (pH adjusted to 7.0 with $NH_3.H_2O$). The mobile phase was delivered by two Altex 100A (Altex Scientific, Berkeley, Calif., U.S.A.) pumps at a total flow rate of 0.4 ml/min and mixed with the injected sample in a mixing chamber before reaching the column and flow-through cell. A Chrompack (Raritan, N.J., U.S.A.) reversed phase $C_{18}$ column was modified to allow the observation of the separation. The injection valve was a pneumatically operated Rheodyne model 7126 with a 10 μl sample loop. The data collection started 70 seconds after sample injection at a rate of 1 spectrum/second for a total of 30 seconds. The spectra were collected in the 200–300 nm range at 2 nm steps.

Figure 11:
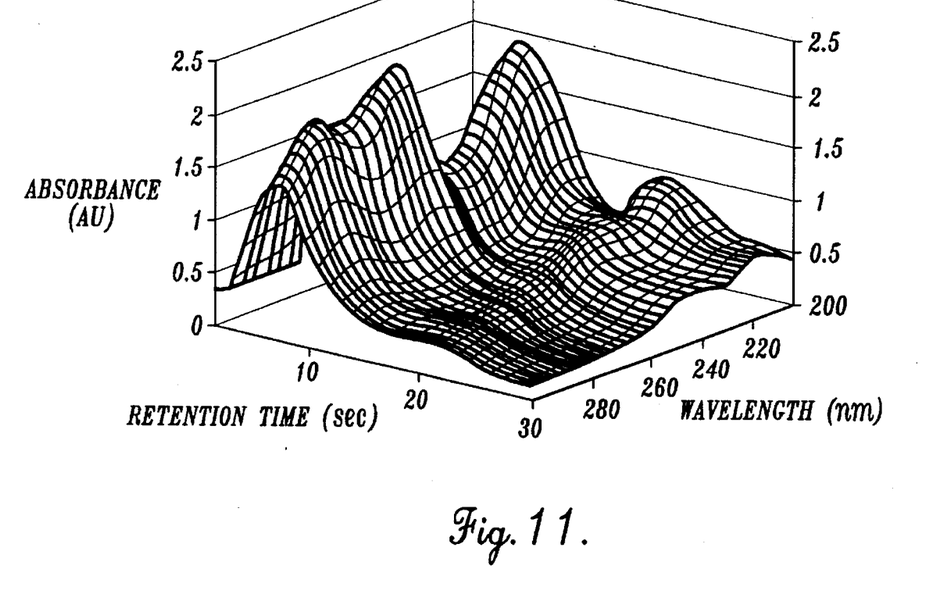
FIG. 11 is the response of a LCUV instrument to a standard sample.
Figure 12:
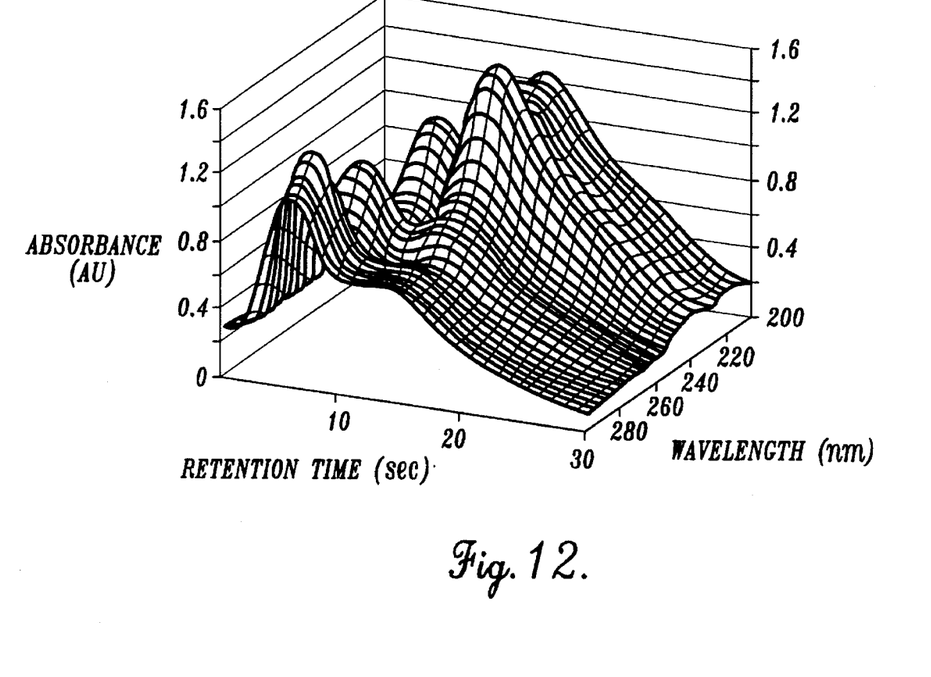
FIG. 12 is the response of the LCUV instrument to a test sample.
Figure 13:
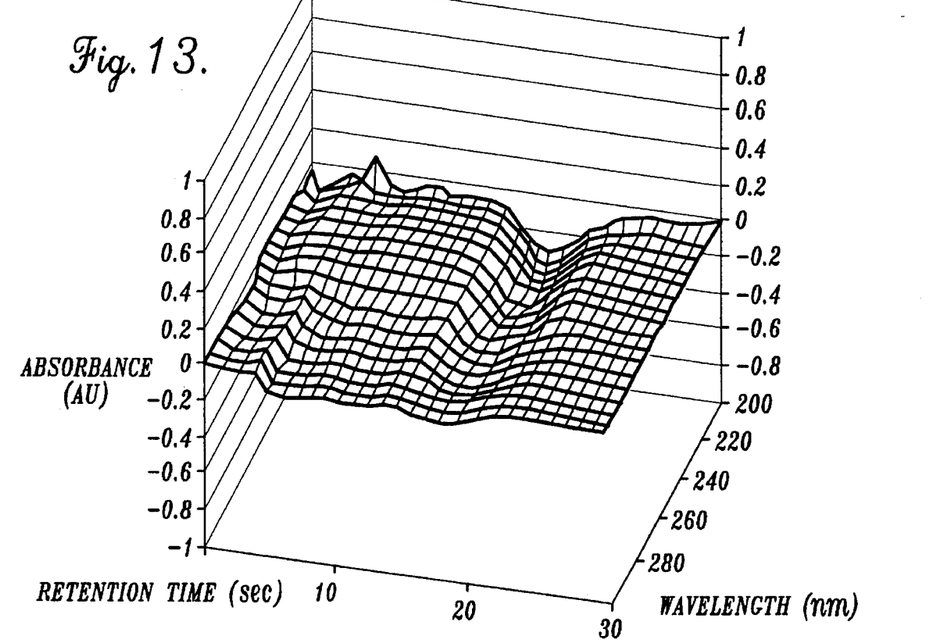
FIG. 13 is the difference in the responses of the standard sample between two separate runs.
Figure 14:
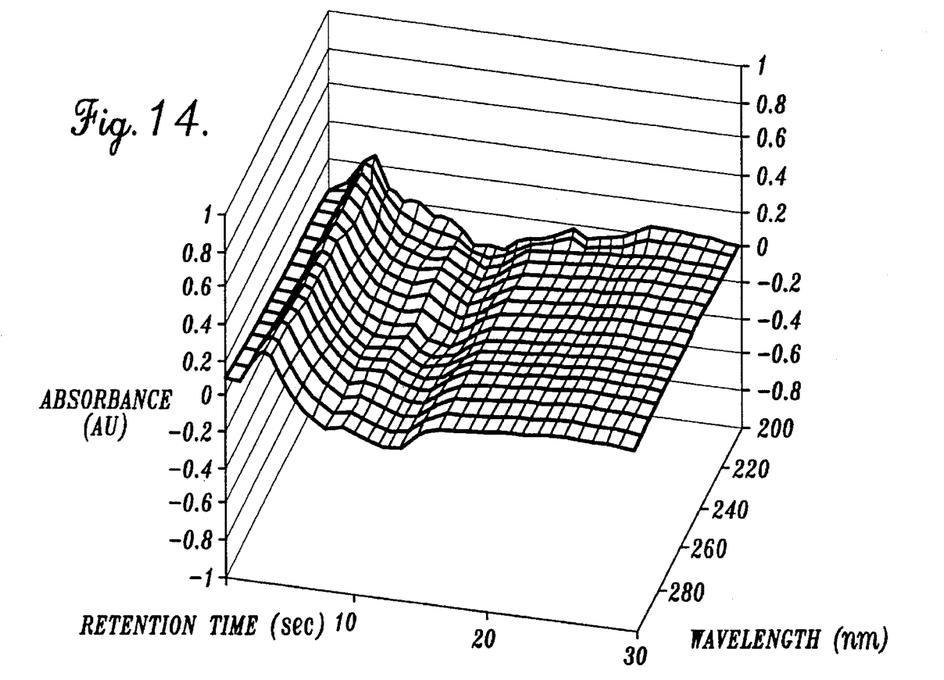
FIG. 14 is the difference in the responses of the test sample between two separate runs.

Four 100 mg/l solutions of FD&C red dye #40, blue dye #2, yellow dye #5, and yellow dye #6 were prepared with HPLC grade water and were then used to prepare two mixtures. The first mixture was prepared by taking 7 ml each of the red dye #40, blue dye #2, and yellow dye #5 solutions and diluting to 25 ml with water; this first mixture serves as the standard sample for standardization. The other mixture was prepared by taking 2 ml red dye #40 solution, 5 ml blue dye #2 solution, and 7 ml yellow dye #6 solution and diluting to 25 ml to serve as the test sample for the standardization. In the experiment, a 50 μl sample was injected to fill the sample loop. After the injection of these two samples, the flow-through cell was taken out of the spectrometer. No effort was made to align the flow-through cell in the next run of the same two samples made one week later. The responses of the two samples measured during the first run are shown in FIGS. 11 and 12. When these two samples were measured during the second run, the responses were significantly different (shown in FIGS. 13 and 14). The average difference between the responses of the same sample is around 0.15 AU. Such a dramatic difference would make it impossible to compare and utilize the measurements conducted at a different time.

Figure 15:
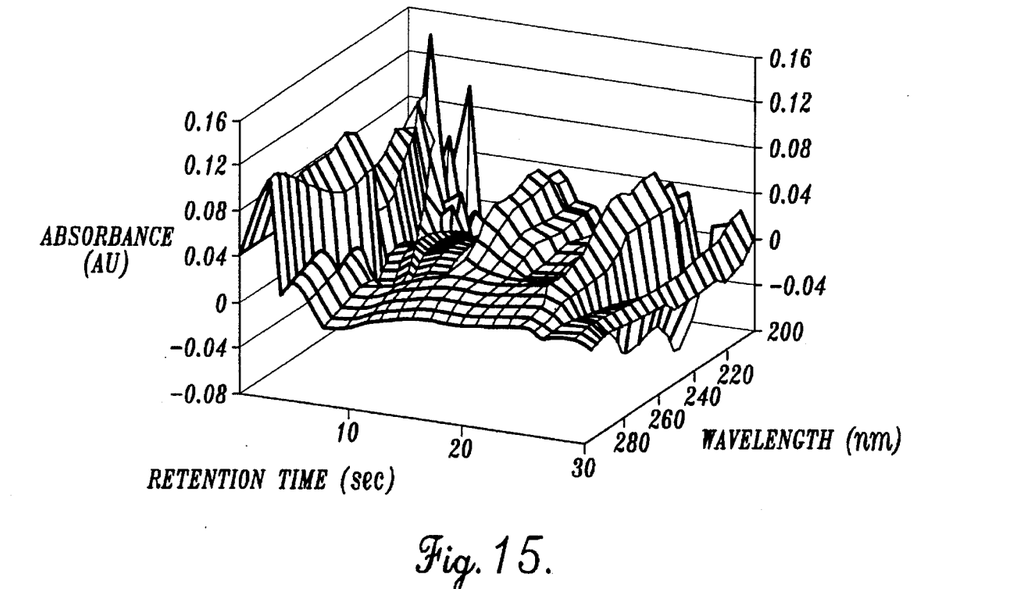
FIG. 15 is the residual matrix of the standard sample after standardization.

Since the time-dependent response variation in the LCUV experiment comes mainly from the chromatographic part of the instrument, the band chosen for B (spectral order) in the standardization is [0 0], and that chosen for A (chromatographic order) is [−1 1]. FIG. 15 shows the difference in the standard sample responses after standardization. It is seen that the difference after standardization is centered around and close to zero in magnitude, indicating that a sufficient model has been attained. However, the residual also shows some clear patterns. There appears to be three bands in the residual, centered around 2, 12, and 20 seconds in retention time. Referring back to the standard response shown in FIG. 11, it becomes clear that the response around 12 seconds is close to zero and the response around 2 and 20 seconds corresponds to three similar chromatographic peaks with similar spectral features. This response pattern will lead to a relatively low local rank and unstable parameter estimations. In spite of this clear pattern, the mean standard error calculated from the difference in the responses has been reduced from about 0.15 (without standardization) to 0.025 after standardization.

Figure 16:
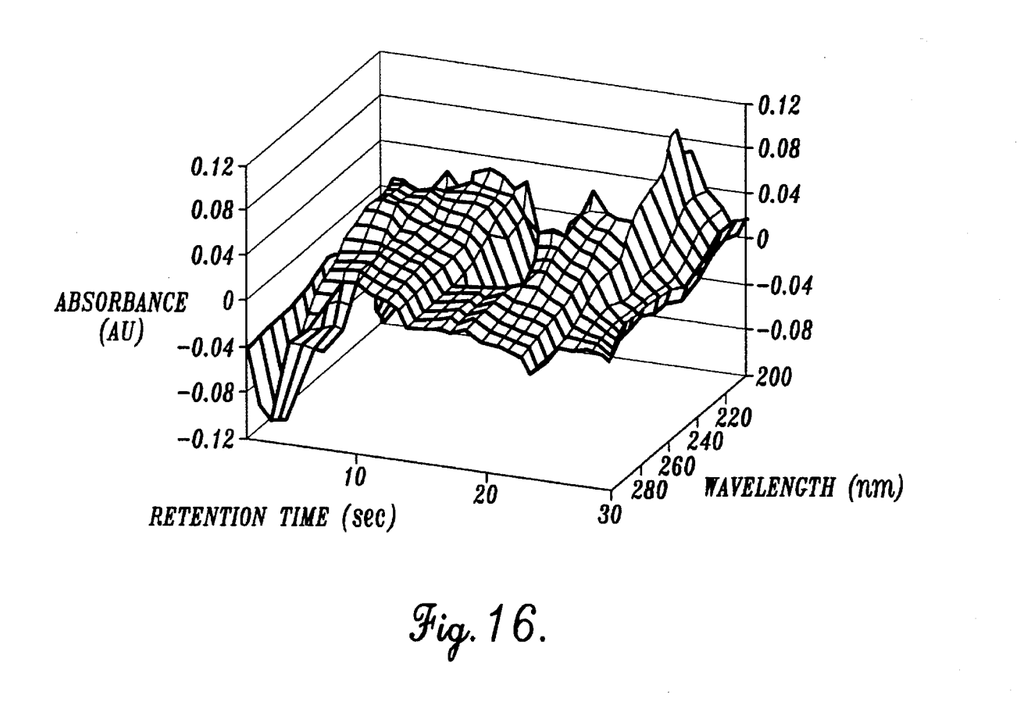
FIG. 16 is the residual matrix of the test sample after standardization.

For similar reasons, the residual after standardizing the test sample (FIG. 16) also shows a pattern around the three retention times mentioned above. The overall trend of the residual is nevertheless centered around and close to zero. The standard error from standardization is about 0.03. With a better designed standard sample, these clear patterns in the residual can be eliminated and the standardization performance improved.

The foregoing demonstrates the applicability of the second order standardization method. The computer simulation has indicated the capacity of second order standardization in modeling both the nonlinear shifts and nonlinear intensity changes, with a relatively small bandwidth for the right and left transformations. In both the computer simulation and the LCUV experimental data study, the extreme importance of the design of the standard sample is observed. On the other hand, the selection of bands in the transformation matrices can be flexible within a certain range with relatively stable standardization performance.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A method of calibrating an uncalibrated output from a first spectrometer relative to an output from a second reference spectrometer, said outputs from said first and second reference spectrometers being a two-dimensional matrix of data, the method comprising the steps of:

(a) calculating a first banded diagonal transformation matrix, said first banded diagonal transformation matrix depending upon the output provided by said second reference spectrometer in response to a standard sample and the output provided by said first spectrometer in response to said standard sample;

(b) calculating a second banded diagonal transformation matrix, said second banded diagonal transformation matrix depending upon the output provided by said second reference spectrometer in response to said standard sample and the output provided by said first spectrometer in response to said standard sample; and (c) multiplying said first and second banded diagonal transformation matrices with said uncalibrated output from said first spectrometer in response to a subsequent sample to provide a calibrated output.

2. The method of claim 1, wherein said first and second banded diagonal transformation matrices are calculated simultaneously using a non-linear least squares operation.

3. The method of claim 2, wherein said non-linear least squares operation is a Gauss-Newton method.

4. A method of calibrating an uncalibrated output from a first chromatograph relative to an output from a second reference chromatograph, said outputs from said first and second reference chromatograph being a two-dimensional matrix of data, the method comprising the steps of:

(a) calculating a first banded diagonal transformation matrix, said first banded diagonal transformation matrix depending upon the output provided by said second reference chromatograph in response to a standard sample and the output provided by said first chromatograph in response to said standard sample;

(b) calculating a second banded diagonal transformation matrix, said second banded diagonal transformation matrix depending upon the output provided by said second reference chromatograph in response to said standard sample and the output provided by said first chromatograph in response to said standard sample; and (c) multiplying said first and second banded diagonal transformation matrices with said uncalibrated output from said first chromatograph in response to a subsequent sample to provide a calibrated output.

5. The method of claim 4, wherein said first and second banded diagonal transformation matrices are calculated simultaneously using a non-linear least squares operation.

6. The method of claim 5, wherein said non-linear least squares operation is a Gauss-Newton method.

7. A method of calibrating an uncalibrated output from a first second order instrument relative to an output from a second second order instrument, said outputs from said first and second instruments being a two-dimensional matrix of data, the method comprising the steps of:

(a) calculating a first banded diagonal transformation matrix, said first banded diagonal transformation matrix depending upon the output provided by said second instrument in response to a standard sample and the output provided by said first instrument in response to said standard sample;

(b) calculating a second banded diagonal transformation matrix, said second banded diagonal transformation matrix depending upon the output provided by said second instrument in response to said standard sample and the output provided by said first instrument in response to said standard sample; and (c) multiplying said first and second banded diagonal transformation matrices with said uncalibrated output from said first instrument in response to a subsequent sample to provide a calibrated output.

8. The method of claim 7, wherein said first and second banded diagonal transformation matrices are calculated simultaneously using a non-linear least squares operation.

9. The method of claim 8, wherein said non-linear least squares operation is a Gauss-Newton method.

* * * * *

UNITED STATES PATENT AND TRADEMARK OFFICE
CERTIFICATE OF CORRECTION

PATENT NO. : 5,559,728
DATED : September 24, 1996
INVENTOR(S) : B.R. Kowalski et al.

It is certified that error appears in the above-indentified patent and that said Letters Patent is hereby corrected as shown below:

| COLUMN | LINE | |
|---|---|---|
| 1 | 4 | Insert the following paragraph after the title: --This invention was made with government support under grant number EEC84-15075 awarded by the National Science Foundation. The government has certain rights in the invention.-- |

Signed and Sealed this

Twenty-fifth Day of March, 1997

Attest:

BRUCE LEHMAN

*Attesting Officer*     *Commissioner of Patents and Trademarks*